United States Patent [19]

Dost et al.

[11] 4,260,631

[45] Apr. 7, 1981

[54] ORAL ADMINISTRATION OF SALINOMYCIN TO PIGS

[75] Inventors: Günter Dost, Kelkheim; Fritz Bauer, Bad Soden am Taunus, both of Fed. Rep. of Germany

[73] Assignee: Hoechst Aktiengesellschaft, Frankfurt am Main, Fed. Rep. of Germany

[21] Appl. No.: 56,197

[22] Filed: Jul. 10, 1979

Related U.S. Application Data

[63] Continuation of Ser. No. 290,602, Apr. 25, 1977, abandoned.

[30] Foreign Application Priority Data

Apr. 27, 1976 [DE] Fed. Rep. of Germany ....... 2618269

[51] Int. Cl.³ .............................................. A61K 31/34
[52] U.S. Cl. .................................................... 424/283
[58] Field of Search ......................................... 424/283

[56] References Cited

U.S. PATENT DOCUMENTS

| | | | |
|---|---|---|---|
| 3,857,948 | 12/1974 | Tanaka et al. | 424/283 |
| 3,947,586 | 5/1974 | Messersmith | 424/283 |
| 4,027,034 | 5/1977 | Messersmith | 424/283 |
| 4,085,224 | 9/1976 | Berg et al. | 424/283 |
| 4,137,241 | 1/1979 | Lin et al. | 424/283 |
| 4,192,887 | 3/1980 | Cloyd et al. | 424/283 |

*Primary Examiner*—John D. Randolph
*Attorney, Agent, or Firm*—Curtis, Morris & Safford

[57] ABSTRACT

Agents containing Salinomycin for oral administration to domestic animals which do not digest cellulose in the rumen, particularly pigs, are disclosed, for instance for the prophylactic treatment of disease and/or for improvement of growth.

14 Claims, No Drawings

ORAL ADMINISTRATION OF SALINOMYCIN TO PIGS

This is a continuation of application Ser. No. 790,602, filed Apr. 25, 1977 and now abandoned.

The present invention relates to an agent to be administered orally to domestic animals which do not have a cellulose digestion in the rumen.

The present invention also relates to the use of Salinomycin for domestic animals not having a cellulose digestion in the rumen, especially pigs, for the prophylaxis and therapy of disturbances in the gastro-intestinal tract by bacterial infections, and also to obtain an improved growth as well as an improved nutrient efficiency. It provides further the agents containing Salinomycin to be administered orally to these animals, as well as a process for their preparation.

Gastro-intestinal infections play an important part in domestic animals and especially in young animals, such as piglets, and lead to considerable economic losses. Alterations of the gastro-intestinal flora caused by a change of feed, but also specific bacterial germs, are etiologically important and lead clinically to diarrhea diseases. An especially feared disease, which involves heavy losses, is the dysentery of pigs caused by *Treponema hyodysenteriae.*

For many years, numerous antibiotics and chemotherapeutical agents have been used for the prophylaxis and therapy of these gastro-intestinal infections, of which there are to be mentioned, above all, tetracyclines, aminoglycoside antibiotics, macrolide antibiotics, nitrofurans, 5-nitro-imidazoles, and acridines. The success has in many cases been unsatisfactory, since resistant strains of germs have increasingly appeared and *Treponema hyodysenteriae* above all is not, or not to a sufficient degree, influenced by the known therapeutic agents.

It has now been found that Salinomycin shows a particularly good effect against dysentery infections in domestic animals without cellulose digestion in the rumen, that it has a greater influence on the germ of the dysentery of pigs than the preparations used so far, and, moreover, that it shows a remarkable growth-stimulating effect.

As physiologically acceptable salts and esters to be used according to the invention instead of, or together with, Salinomycin, there are used, for example, alkali metal salts, especially the sodium, potassium or ammonium salts, alkaline earth metal salts, particularly the magnesium or calcium salts, and alkyl esters, especially those having from 1 to 8, preferably from 1 to 4 carbon atoms, as well as benzylester.

As domestic animals not having a cellulose digestion in the rumen there are considered preferably agricultural livestock, in particular mammals, preferably pigs.

Salinomycin, its salts and esters have been described, for example in British Pat. No. 1,378,413 and in German Offenlegungsschrift No. 2 353 998. In these places, its use as anticoccidiosis agent has also been mentioned.

In "The Journal of Antibiotics" XXVII, 11, 814–821 (1974), the antibacterial spectrum of activity and the action intensity of Salinomycin have also been described, inter alia, in which case only an insignificant or moderate effect against the specified microorganisms has been found.

The particular effectiveness of the said substance in the prophylaxis and therapy of gastro-intestinal infections in domestic animals without cellulose digestion in the rumen, the excellent effect on *Treponema hyodysenteriae*, the germ of the dysentery of pigs, and also the growth-stimulating effect in domestic animals without a rumen digestion were therefore surprising and could not have been foreseen.

In order to detect the surprising effect on *Treponema hyodysenteriae*, this microorganism was cultivated according to the method of Harris on a trypticase-soy-agar using an addition of horse blood of 5% in a $CO_2/H_2$ atmosphere, and the minimum inhibiting concentration of Salinomycin was determined in the agar diffusion test, while using the corresponding dilution series, as compared against commercial preparations showing a particularly good effect in dysentery diseases.

Table 1 shows the superior effect of Salinomycin.

TABLE 1

|  | Minimum inhibiting concentration (MIC) in mcg/ml |
|---|---|
| Tetracycline-HCl | 50 |
| Oxytetracycline | 100 |
| Erythromycin | >100 |
| Tylosin | >100 |
| 3,6-Diamino-10-methyl-acridinium chloride | 100 |
| Ethacridine lactate | 100 |
| Dimethridazol | 5 |
| Ipronidazol | 2 |
| Salinomycin | 0.05 |

According to the invention, Salinomycin may be administered as the pure substance, as a raw product, or as a mycelium.

For commercial reasons it may be advantageous not to use the pure substance, but the mycelium, especially in the case of an addition to the feed.

It is possible to add the agents used according to the invention, for example, to the supplementary feed or to the all-mash feed, or only to part of the daily feed ration. Generally, an addition to the mixed feed will be preferred.

A preferred method of administering the active substance is in many cases its addition to the feed in the form of a concentrate (premix). The concentrate may be prepared, for example, by mixing the active substance, the raw product or the mycelium containing the active substance with a physiologically acceptable solid or liquid carrier. As solid carriers there may be mentioned, for example, by-products of cereals, such as wheat flour of inferior quality, wheat bran or de-oiled rice bran, but also corn meal, soy meal, bolus alba or calcium carbonate. As liquid carriers, there may be used physiological salt solutions, distilled water and physiologically acceptable organic solvents. It is also possible to add suitable additives, such as emulsifying agents, dispersing agents, wetting agents or gelatinizing agents. These concentrates may contain as a rule from about 0.5 to about 5% of the active substance, however the concentration of this substance may also be considerably higher or lower, depending on the purpose of application.

For administering the active substances together with feeding stuffs, a concentrate is suitably mixed with the feed by grinding, shaking, stirring. The use of a powdery concentrate has proved to be particularly useful for being mixed with feed.

Another method of administering the active substance consists in adding said substance as such or in the form of a concentrate or suspendable powder to the drinking water or another drink, for example, milk replacer.

The feed to which the active substance is to be added in accordance with the invention comprises the common feeding stuffs, for example, cereals, such as corn, wheat, barley, oats as well as soy meal, other oilseed meals, fish meal and mixed feed prepared from the above ingredients, supplementary feed or mixtures of mineral substances.

The mixing with the feed may also be effected in a way that a substance of the invention is administered directly orally to the animals before, during or after feeding, for example in the form of a solid or liquid galenic preparation, such as a tablet, a capsule, a paste, granules, a powder, a bolus, a juice or syrup, or in the form of a concentrate mentioned above. In this way the mixing with the feed—which is important according to the invention—is effected immediately after the application in the stomach, thus producing the effect of a considerably improved nutrient efficiency and an increased growth according to the invention in the same manner.

Especially in the case of a controlled diarrhea treatment or prophylaxis, the administration in the form of such galenic preparations can be of particular interest.

For the administration in the form of tablets, capsules, pastes, boli, pills, granules, juices, syrups, etc., the same auxiliary agents and additives may be added, as are commonly known for galenic preparations from pharmaceutical technology. The active substances may be mixed, for example, with powdery diluents, such as microcrystalline cellulose, sugar or starch for filling up the volume of the capsule. The preparation of the tablets may also be performed in common manner, while adding substances, for example, cellulose, lactose, sodium chloride, starch, surface-active agents, such as sodium laurylsulfate, binding agents, such as gelatin, starch, dextrin, cellulose derivatives, etc. For the preparation of liquid formulations, use may also be made of the auxiliary agents which are common in pharmacy, such as vegetable oils, collidone, cellulose derivatives, inter alia auxiliary dispersing agents or emulsifying agents, water, etc. An aqueous suspension of Salinomycin may for example contain, besides Salinomycin, raw product or ground mycelium, carboxymethyl cellulose, collidone 25, Aerosil, appropriate buffer substances, and water.

Combinations with other antibiotics and chemotherapeutical agents, such as, for example, sulfonamides, nitrofurans, quinoxaline-N-oxides, 5-nitro-imidazoles, tetracyclines, aminoglycoside and macrolide antibiotics, Flavomycin and/or Virginiamycin or arsenicals are also possible, especially for the broadening of the spectrum of activity.

Depending on the indication and the kind of application, the dosage may be in the range of from about 0.02 to about 5.0, preferably from about 0.2 to about 2.0 mg of the active substance used according to the invention per kg of body weight and day. This results in a concentration in the feed of from about 0.5 to 500, preferably from about 2 to 100 g of active substance per ton.

Depending on the animal species and the age of the animals, galenic preparations may contain, for example, from about 4 to 400, preferably from about 10 to 100 mg of active substance per dosage unit, by which unit there is to be understood, for example, a tablet, a capsule, a bolus, etc.; concentrates (premixes) may contain, for example, concentrations in the range of from about 0.1 to 10%, preferably from about 1 to 5% of active substance. The above-mentioned dosage limits may easily be exceeded in appropriate cases.

The following Examples serve to illustrate the invention.

EXAMPLE 1

A feeding test using Salinomycin was carried out on 78 piglets which were kept in boxes with 4 (or 3) animals each. At the beginning of the test, the animals were about 4 weeks old. Four replicates formed one group, and the following treatments were carried out:

1st group: untreated control group
2nd group: Salinomycin as raw product: 25 mg/kg of fodder
3rd group: Salinomycin as raw product: 50 mg/kg of fodder
4th group: Salinomycin as mycelium: 50 mg/kg of fodder
5th group: comparison preparation A: 50 mg/kg of fodder (5-Nitromidazol)

The basic feed had the following composition:

| | |
|---|---|
| Fish meal | 5% |
| coarse meal of linseed cake | 5% |
| coarse meal of soybean | 25% |
| coarse meal of barley | 50% |
| wheat bran | 11% |
| CaCO$_3$ | 2% |
| Na-Mg-Ca-phosphate | 1% |
| NaCl | 0.6% |
| mixture of trace elements | 0.2% |
| vitamin premix | 0.2% |
| | 100% |
| Total nutrients | 660 |
| Digestible protein | 19.2% |

The occurrence of diarrhea in the individual boxes (sub-groups) was registered in the test periods of 14 days each and in the total test run of 56 days. Table 2 shows the "diarrhea days" of each test group in absolute figures and as percent of the respective test days. Of a total of 224 test days, for example, the control animals showed diarrhea on 185 days (=82.6%), whereas the test group using 50 mg of Salinomycin (as mycelium) per kg of feed showed diarrhea only on 24 days (=10.7%). Salinomycin was found to have a very good influence on the incidence of diarrhea depending on the dosage, as compared against the untreated control and a comparison preparation.

EXAMPLE 2

A feeding test using Salinomycin as a raw product was carried out on 46 piglets weaned at an early age (4 weeks old) that were kept in sub-groups comprising 3 or 4 animals.

Initial weight: 9.8 kg on an average. The feed ration indicated in Example 1 served as basic feed.

4 Sub-groups comprising 15 animals altogether formed the untreated control group. 4 Sub-groups comprising 16 animals altogether were given 25 mg of Salinomycin as raw product per kg of feed, and 4 sub-groups comprising 15 animals altogether were given 50 mg of Salinomycin per kg of feed in the form of the raw product. The test period was 8 weeks, with individual weighing at intervals of 2 weeks.

Results:

Table 3 shows as a comparison the weight gain and the feed efficiency in the control group and the test groups. The improvement obtained by 25 mg of Salinomycin per kg of feed could be covered statistically with a significance of 99%, and the improvement obtained by 50 mg of Salinomycin per kg of feed was shown even with a significance of 99.9%.

TABLE 2

Piglet test S 83/75 for examining the incidence of diarrhea
4 Stalls with 14 test days = 56 days per test period (= 100%)
4 Test periods with 56 days = 224 days altogether (= 100%)

| Group. No. | Stall No. | No. of animals | | 1st and 2nd week | 3rd and 4th week | 5th and 6th wk. | 7th and 8th wk. | 1st through 8th week |
|---|---|---|---|---|---|---|---|---|
| Control | 1 | 15 | days | 33 | 49 | 54 | 49 | 185/224 |
| | 12 | | | | | | | |
| | 25 | | | | | | | |
| | 34 | | % | 58.9 | 87.5 | 96.4 | 87.5 | 82.6 |
| Salinomycin raw | 2 | | days | 27 | 26 | 39 | 43 | 135/224 |
| | 11 | | | | | | | |
| pr. dos. 25 ppm | 24 | 16 | | | | | | |
| | 35 | | % | 48.2 | 46.6 | 69.6 | 76.8 | 60.3 |
| Salinomycin raw | 3 | | days | 7 | 7 | 16 | 13 | 43/224 |
| | 14 | | | | | | | |
| pr. dos. 50 ppm | 21 | 15 | | | | | | |
| | 36 | | % | 12.5 | 12.5 | 28.6 | 23.2 | 19.1 |
| Salinomycin as mycelium, 10% activity | 4 | | | | | | | |
| | 13 | | | | | | | |
| | 26 | 16 | days | 11 | 3 | 4 | 6 | 24/224 |
| dos. 50 ppm | 31 | | % | 19.6 | 5.4 | 7.1 | 10.7 | 10.7 |
| Prep. A (5-Nitro-imidazol) | 6 | | days | 20 | 22 | 41 | 39 | 122/224 |
| | 15 | 16 | | | | | | |
| | 22 | | | | | | | |
| dos. 50 ppm | 23 | | % | 35.7 | 39.3 | 73.2 | 69.6 | 54.5 |

TABLE 3

Effect of Salinomycin (as raw product) on the growth and the feed efficiency in piglets weaned early (4 weeks old)

| | Test weeks | Control initial weight 9.8 kg n = 15 absolute | Salinomycin 25 ppm init. wt. 9.8 kg n = 16 abs. | rel. | Salinomycin 50 ppm init. wt. 9.8 kg n = 15 abs. | rel. |
|---|---|---|---|---|---|---|
| Weight gain per animal in kg | 2 | 2.3 | 2.4 | 104.3% | 2.4 | 104.3% |
| | 4 | 6.7 | 7.0 | 104.6 | 7.2 | 107.5 |
| | 6 | 12.6 | 13.0 | 103.3 | 13.8 | 109.8 |
| | 8 | 20.5 | 21.3 | 103.8++ | 22.2 | 108.2+++ |
| Daily weight gain p. animal in g | 2 | 164 | 171 | — | 171 | — |
| | 4 | 239 | 250 | — | 257 | — |
| | 6 | 307 | 317 | — | 337 | — |
| | 8 | 366 | 380 | — | 396 | — |
| Feed efficiency per animal | 2 | 1.983 | 1.900 | 95.8% | 1.900 | 95.8% |
| | 4 | 1.881 | 1.800 | 95.7 | 1.750 | 93.0 |
| | 6 | 1.860 | 1.802 | 96.9 | 1.698 | 91.3 |
| | 8 | 1.972 | 1.898 | 96.2++ | 1.821 | 92.3+++ |

++ = 99% significance
+++ = 99.9% significance

EXAMPLE 3

A feeding test using Salinomycin as a mycelium was carried out on 47 piglets weaned at an early age (4 weeks old) which were kept in sub-groups comprising 4 and 3 animals, respectively. The initial weight was 9.8 kg on an average. The feed ration indicated in Example 1 served as basic feed.

4 Sub-groups comprising 15 animals altogether formed the untreated control group. 4 Sub-groups comprising 16 animals altogether were given 50 mg of Salinomycin as a mycelium per kg of feed, and 4 sub-groups comprising 16 animals altogether were given 50 mg of a comparison preparation A (5-Nitroimidazol) per kg of feed. The test period was 8 weeks, with individual weighing at intervals of 2 weeks.

Results:

Table 4 shows as a comparison the weight gain and the feed efficiency in the individual groups. The improvement of the weight development obtained by 50 mg of Salinomycin per kg of feed could be covered statistically with a significance of 99.9% after a test period of 8 weeks, and the improvement of the feed efficiency with a significance of 99%. In contradistinction thereto, the effect of the comparison preparation could not be covered.

TABLE 4

Effect of Salinomycin (as mycelium) on the growth and the feed efficiency in piglets weaned early (4 weeks old)

| | Test weeks | Control initial wt. 9.8 kg n = 15 absolute | Salinomycin 50 ppm init. wt. 9.8 kg n = 16 abs. | rel. | Preparation A 50 ppm n = 16 abs. | rel. |
|---|---|---|---|---|---|---|
| Weight gain p. animal in kg | 2 | 2.3 | 2.3 | 100.0% | 2.5 | 109.1% |
| | 4 | 6.7 | 7.3 | 109.2 | 7.0 | 104.6 |
| | 6 | 12.6 | 13.6 | 108.1 | 13.2 | 104.9 |
| | 8 | 20.5 | 22.0 | 107.4+++ | 20.9 | 101.9 |
| Daily weight gain p. animal in g | 2 | 164 | 164 | — | 179 | — |
| | 4 | 239 | 261 | — | 250 | — |
| | 6 | 307 | 332 | — | 322 | — |
| | 8 | 366 | 393 | — | 373 | — |
| Feed efficiency p. animal | 2 | 1.983 | 1.983 | 100.0% | 1.824 | 92.0% |
| | 4 | 1.881 | 1.726 | 91.8 | 1.800 | 95.7 |
| | 6 | 1.860 | 1.723 | 92.6 | 1.775 | 95.4 |
| | 8 | 1.972 | 1.837 | 93.2++ | 1.934 | 98.1 |

++ = 99% significance
+++ = 99.9% significance

What is claimed is:

1. The method for improving the growth and nutrient efficiency of pigs free of swine dysentery, which method comprises orally administering thereto an effective amount of an active agent selected from the group consisting of Salinomycin, physiologically acceptable salts thereof, and physiologically acceptable esters thereof.

2. The method as in claim 1 wherein from about 0.02 mg to 5.0 mg of said active agent is administered per day per kg of body weight.

3. The method as in claim 1 wherein said active agent is administered in combination with a feeding substance.

4. The method as in claim 3 wherein said active agent is presented in said feeding substance in a concentration from 0.5 g to 500 g per ton.

5. The method as in claim 1 wherein said active agent is administered in combination with a supplemental feed.

6. The method as in claim 5 wherein said active agent is present in a concentrate at a concentration from about 0.1 percent to 10 percent.

7. The method as in claim 1 wherein said active agent is administered in combination with a pharmaceutical auxiliary.

8. The method as in claim 7 wherein said active agent is present with said pharmaceutical auxiliary in an amount from about 4 mg to 400 mg per dosage unit form.

9. The method as in claim 1 wherein Salinomycin is administered as a salt or ester thereof, or as a mixture of a salt and ester thereof.

10. The method as in claim 1 wherein Salinomycin is administered as an alkali metal or alkaline earth metal salt thereof.

11. The method as in claim 1 wherein Salinomycin is administered as its sodium, potassium, ammonium, magnesium, or calcium salt.

12. The method as in claim 1 wherein Salinomycin is administered as a $C_1$-$C_2$ alkyl ester or as the benzyl ester thereof.

13. The method as in claim 1 wherein Salinomycin is administered as mycelium or raw product.

14. The method as in claim 1 wherein said active agent is administered in drinking water, some other drink, or in a liquid feeding substance.

* * * * *

UNITED STATES PATENT AND TRADEMARK OFFICE
CERTIFICATE OF CORRECTION

PATENT NO. : 4,260,631

DATED : April 7, 1981

INVENTOR(S) : Gunter Dost et al.

It is certified that error appears in the above—identified patent and that said Letters Patent is hereby corrected as shown below:

On the Title Page, Item (63), "Continuation of Ser. No. 290,602" should read -- Continuation of Ser. No. 790,602 --.

Signed and Sealed this

Eighteenth Day of August 1981

[SEAL]

Attest:

GERALD J. MOSSINGHOFF

Attesting Officer   Commissioner of Patents and Trademarks